United States Patent [19]

Jelly

[11] Plant 4,408

[45] Apr. 17, 1979

[54] WHITE ROSE SEEDLING

[75] Inventor: Robert G. Jelly, Richmond, Ind.

[73] Assignee: E. G. Hill Co., Inc., Richmond, Ind.

[21] Appl. No.: 911,444

[22] Filed: Jun. 1, 1978

[51] Int. Cl.[2] ..... A01H 5/00

[52] U.S. Cl. ..... Plt./14

[58] Field of Search ..... Plt./14

*Primary Examiner*—Robert E. Bagwill

*Attorney, Agent, or Firm*—Chas. W. Rummler

[57] ABSTRACT

A white rose cultivar intended for cut flower production under greenhouse culture and distinguished by its large double blooms which have a high centered opening form on strong, erect stems of longer length, and by its moderately free and vigorous growth habit.

6 Drawing Figures

BACKGROUND OF THE NEW PLANT

My new variety of rose plant was originated at Richmond, Indiana, as a seedling resulting from my crossing "White Butterfly" (P.P. 1337) with "Promise Me" (P.P. 3167), in the Spring of 1969, with the object of combining the better characteristics of the parents, namely to produce an improved bloom with greater stem length and better growth habit. This new seedling, which first flowered in 1970, reflects the success of this cross and my asexual propagation of this seedling through several generations by grafting at Richmond, Indiana, and by budding at Livermore, California, has demonstrated that the improved characteristics of the new plant hold true from generation to generation and appear to be firmly fixed.

DESCRIPTION OF THE DRAWING

This new variety of rose plant is illustrated by the accompanying photographic drawing which shows, in full color, a face view of a fully opened flower, specimens of buds in several stages of opening, specimens of young and mature wood, and typical leaves. The colors shown are believed to be as nearly true as it is reasonably possible to be obtained through conventional photographic procedures.

DESCRIPTION OF THE NEW PLANT

The following is a detailed description of my new variety of rose plant based upon observations, made in December 1977, of greenhouse plants grown at Richmond, Ind., the color designations being according to the Robert G. Wilson Horticultural Colour Chart (W) and the R.H.S. Colour Chart (RHS), both issued by The Royal Horticultural Society of London, England.

THE PLANT

Origin: Seedling.

Parentage:

*Seed parent.*—White Butterfly (P.P. 1337).

*Pollen parent.*—Promise Me (P.P. 3167).

Classification: Hybrid Tea

Type: Seedling, for greenhouse culture, for cut flowers.

Form: Bush

Growth (In Greenhouse): Moderately free and vigorous.

Habit: Upright and well branched.

Canes: Small to medium in size.

Main Stems: Color — Spinach Green 0960 (W), freckled with Ivy Green 0001060/3 (W).

*Thorns.*—Very few and only on some canes.

*Shape.*—Short and downwardly hooked from a short, narrow base.

*Color.*—Greyed Orange 165B (RHS), pencilled with 165A toward the tip.

*Prickles and Hairs.*—None

Branches: Color — Yellow Green 144B (RHS) background pencilled and dotted with Spinach Green 0960/1 (W).

Thorns: Very few, and only on some of the branches.

*Shape.*—Medium in length, generally straight but hooked slightly downward from a short and narrow base.

*Color.*—Greyed Orange 174D (RHS) at the base, becoming almost translucent at the tip.

*Prickles and Hairs.*—None

Foliage:

*Leaves.*—Odd pinnate, compounded of 3, 5 or 7 leaflets.

*Leaflets.*—Normally of medium size.

*Shape.*—Ovoid, with obtuse base, cuspidate apex and irregularly serrate margins.

*Color.*—Young leaves: Upper Surface — Greyed Red 178A (RHS) along the mid-vein, blending through Yellow Green 144B (RHS) along the border. Under Surface — Green 138B (RHS) along the mid-vein, washed with Greyed Orange 176B (RHS) toward the margin and bordered with Greyed Red 178A (RHS). Mature Leaves: Upper Surface — Green 137A (RHS). Under Surface — A shade between Sage Green 000861/1 (W) and Spinach Green 0960/3 (W).

*Rachis.*—Medium to heavy in size with upper side grooved and prickly. The under side of few have thorns.

*Stipules.*—Medium in width and medium to long in length, with short points that turn outward at an angle of less than 45° and then recurve toward the stem.

THE BUD

Before the Calyx Breaks:

*Bud Size.*—Small.

*Form.*—Short pointed, with a conspicuous neck, with foliaceous appendages on the surface of the bud, and with slender bristle-like foliaceous parts extending beyond the tip of the bud for a distance equal to about ¼ to ½ of the bud length.

*Color of calyx.*—Yellow Green 144B (RHS) at the base, blending to Green 138A (RHS) to Greyed Purple 185C (RHS) at the tip.

As the Calyx Breaks:

*Color of outside petals.*—Pod Green 061/2 (W).

As First Petal Opens:

*Bud Size.*—Medium large.

*Form.*—Moderately long pointed.

*Color.*—Outside Petal — Chartreuse Green 663/2 (W) at point of attachment, blending to Sap Green 62/3 (W). Inside Petal — Green Yellow 1D(RHS) at point of attachment, blending to Chartreuse Green 663/3 (W).

Sepals: Permanent and of medium length.

*Color.*—Inside — Yellow Green 145C (RHS) at the point of attachment, blending through Yellow Green 145B to a shade slightly darker than Spinach Green 0960 (W) at foliaceous parts, and with hairs which are almost translucent at the base becoming Red 45C (RHS) at the tip. Outside — Yellow Green 144B (RHS) at the point of attachment, blending to Green 138A (RHS).

Character of opening: Very well in greenhouse.

Effect of weather: Hot, dry weather causes smaller bud size.

Peduncle:

*Size.*—Long in length and of medium diameter.

*Strength.*—Erect on strong to medium strong stems.

*Bark.*—Almost entirely smooth. Color: Scheeles Green 860 (W) with highlights of Yellow Green 144B (RHS). Thorns: None. Prickles: Numerous. Color: A shade of Greyed Purple 184B (RHS). Hairs: None.

THE FLOWER

Blooming Habit: Free and continuous in greenhouse.

Size of Bloom: Large, 4 to 4-½ inches in diameter when fully opened.

Form: High centered, at first with petals loosely rolled outward and becoming very loosely rolled outward at maturity.

Borne: One to a stem.

Petalage: Double, from 25 to 26 petals, regularly arranged.

*Shape.*—Obovate with mucronate apex and one notch, the inside petals differing by having two notches.

*Texture.*—Moderately thick and leathery.

*Aspect.*—Satiny on both inside and outside surfaces.

Color:

A. The following is the color description of a rose newly opened in December 1977 in greenhouse at Richmond, Ind.

*Outside petals.*—Outer Surface — Sap Green 62/2 (W) at point of attachment, shading to the main color of White 155B (RHS). Inside Surface — Primrose Yellow 601/1 (W) at point of attachment, shading to White 155B (RHS).

*Intermediate petals.*—Outer Surface — Yelow Green 154C (RHS) at point of attachment, blending to White 155A (RHS). Inside Surface — Yellow Green 150C (RHS) at point of attachment, blending to White 155A (RHS).

*Inner petals.*—Outer Surface — Yellow Green 150C (RHS) at point of attachment, blending to Yellow Green 150D (RHS). Inside Surface — Yellow Green 154C (RHS) at point of attachment, blending to a tint slightly lighter than Yellow Green 150D (RHS).

B. This description was made from observation of a rose that had been fully opened for three days in December 1977 in greenhouse at Richmond, Ind.

*Outside petals.*—Outer Surface — Green Yellow 1C (RHS) at point of attachment, blending to White 155B (RHS). Inside Surface — Yellow 6C (RHS) at point of attachment, blending to White 155B (RHS).

*Intermediate petals.*—Outer Surface — Yellow 2D (RHS) at point of attachment, blending to White 155B (RHS). Inside Surface — Yellow 9C (RHS) at point of attachment, shading to White 155B (RHS).

*Inner petals.*—Outer Surface — Yellow 6D (RHS) at point of attachment, blending to Primrose Yellow 601/3 (W). Inside Surface — Yellow 6B (RHS) at point of attachment, blending to Yellow 4D (RHS).

General color effect of open bloom:

*Newly opened flower.*—A shade between Yellow Green 150D (RHS) and White 155B (RHS).

*Three days opened flower.*—White 155B (RHS).

*Note.*—The colors may be modified by being bordered, margined, pencilled, striped, dotted, blotched, shaded, washed, or tinted with other colors.

Fragrance in greenhouse: Penetrating spicy.

Persistence: The petals persist.

Effect of weather: In hot, dry weather, the bud size is slightly smaller and the color intensity fades to White 155D (RHS).

Lasting quality: Flower kept well for eight days at living room temperature in December.

REPRODUCTIVE ORGANS

Stamens: Very many in number, arranged irregularly about the pistils and mixed with petaloids.

Filaments: Short, long and medium, most with anthers.

*Color.*—Shades of Red 47C (RHS) and 47D (RHS) at the base of some, blending to Yellow 3C (RHS) the main color.

Anthers: Medium to large, all opening at once.

*Color.*—The center of the pollen cup is Greyed Orange 163D (RHS), bordered by Greyed Orange 163C (RHS) and Greyed Orange 163A (RHS).

*Pollen.*—Moderate in quantity.

Pistils: Very many in number.

*Styles.*—Uneven, short, long and medium in length, medium heavy, and very bunched.

*Color.*—White 155A (RHS) shaded to Red 53B (RHS) under the stigma.

*Stigma.*—Color — Orange White 159A (RHS).

Ovaries: Some protruding from calyx.

Hips: None available.

Seeds: None available.

This new variety of rose plant is very superior to its seed parent, White Butterfly, in petal texture, length of stem and freedom of growth. This new cultivar is also an improvement over its pollen parent, Promise Me, in its very rapid crop turnover and the longer pointed form of its bud.

A particular advantage possessed by this cultivar is its very free growth habit on erect stems of good strength and the high centered and very fine opening form of its blooms.

I claim:

1. A new and distinct rose cultivar substantially as herein shown and described, characterized by the large size and high centered form of its blooms, the improved length of stems and freedom of growth compared to its seed parent and the improved bud form and rapid crop turnover compared with its pollen parent.

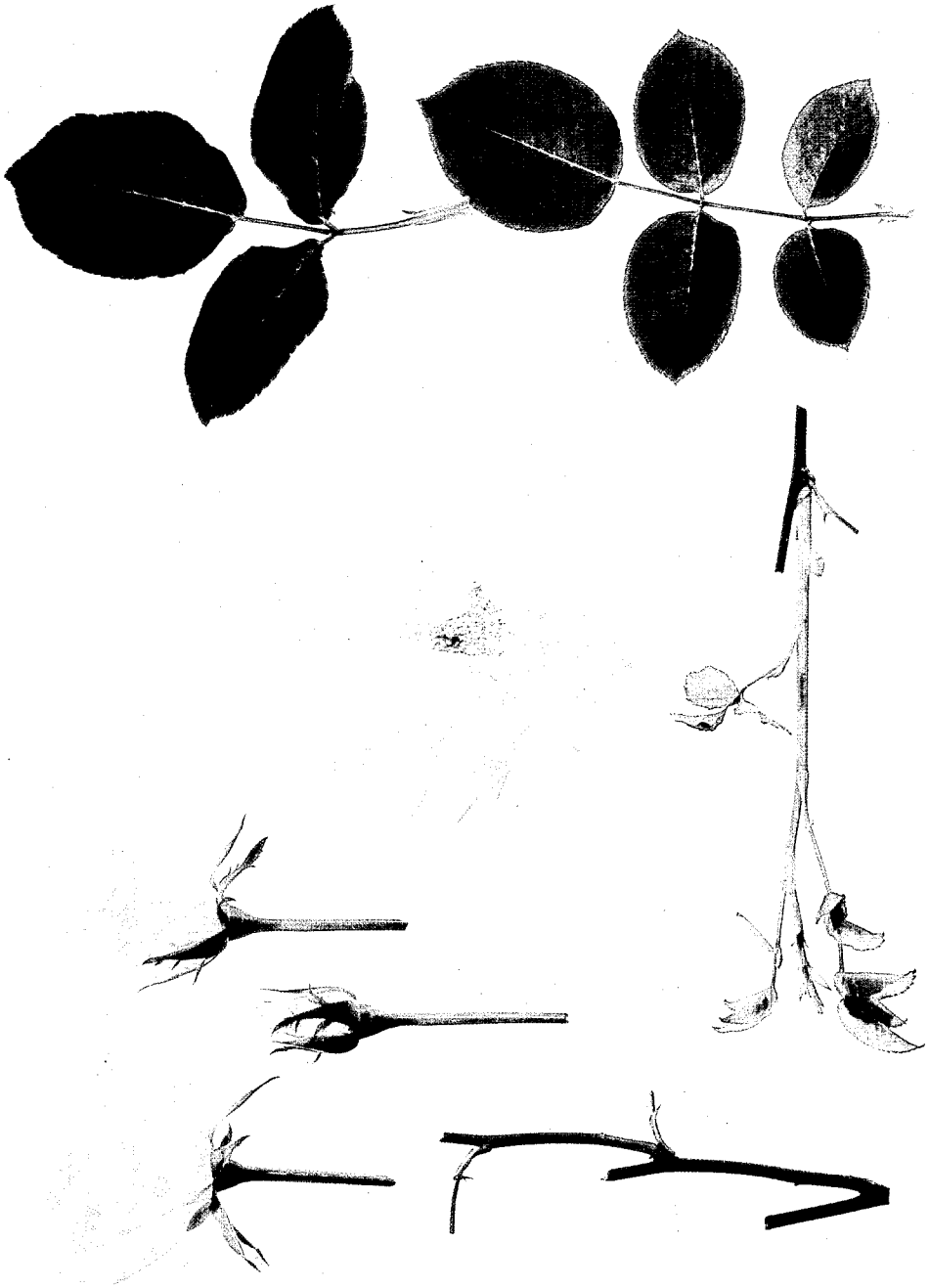

* * * * *